United States Patent
Mesens et al.

(10) Patent No.: US 6,368,632 B1
(45) Date of Patent: *Apr. 9, 2002

(54) MICROENCAPSULATED 3-PIPERIDINYL-SUBSTITUTED 1,2-BENZISOXAZOLES AND 1,2-BENZISOTHIAZOLES

(75) Inventors: Jean Mesens, Wechelderzande (BE); Michael E. Rickey, Loveland, OH (US); Thomas J. Atkins, York, PA (US)

(73) Assignees: Janssen Pharmaceutica, Beerse (BE); Alkermes Controlled Therapeutics Inc. II, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/578,908

(22) Filed: May 26, 2000

Related U.S. Application Data

(63) Continuation of application No. 09/252,486, filed on Feb. 18, 1999, now Pat. No. 6,110,921, which is a continuation of application No. 09/005,549, filed on Jan. 12, 1998, now Pat. No. 5,965,168, which is a continuation of application No. 08/808,261, filed on Feb. 28, 1997, now Pat. No. 5,770,231, which is a continuation of application No. 08/154,403, filed on Nov. 19, 1993, now abandoned.

(51) Int. Cl.[7] .............................. A61K 9/14; A61K 9/50; A01N 43/54

(52) U.S. Cl. ...................... 424/489; 424/486; 424/497; 424/501; 514/258; 514/964; 514/965

(58) Field of Search .................................. 424/497, 486, 424/489, 501; 514/258, 964, 965

(56) References Cited

U.S. PATENT DOCUMENTS

| | | |
|---|---|---|
| 3,197,180 A | 7/1965 | Bates et al. |
| 3,523,906 A | 8/1970 | Vrancken et al. |
| 3,691,090 A | 9/1972 | Kitajima et al. |
| 3,737,337 A | 6/1973 | Schnoring et al. |
| 3,773,919 A | 11/1973 | Boswell et al. |
| 3,891,570 A | 6/1975 | Fukushima et al. |
| 3,923,288 A | 12/1975 | King et al. |
| 3,960,757 A | 6/1976 | Morishita et al. |
| 4,034,965 A | 7/1977 | King et al. |
| 4,111,402 A | 9/1978 | Barbini et al. |

(List continued on next page.)

FOREIGN PATENT DOCUMENTS

| | | |
|---|---|---|
| EP | 0 052 510 | 5/1982 |
| EP | 0 071 454 | 2/1983 |
| EP | 0 129 619 | 1/1985 |

(List continued on next page.)

OTHER PUBLICATIONS

Abstract of WO 94/10982, Kino et al., "Sustained–release Microspheres Requiring No Surgical Implant—Contains Hydriophobic Antipsychotic Encapsulated in Biodegradable Polymer, Allowing Prolonged Therapeutic Effect by Infrequent Administration". (1994).

Baker, J.R., "Motionless Mixers Stir Up New Uses," *Chemical Engineering Progress*: 32–38 (Jun. 1991).

Borison, R.L. et al., Clinical Overview of Risperidone, in: Meltzer, H., Y., ed., *Novel Antipsychotic Drugs*, Raven Press, Ltd., N.Y.: 233–239 (1992).

(List continued on next page.)

*Primary Examiner*—Floyd D. Higel
*Assistant Examiner*—Ebenezer Sackey
(74) *Attorney, Agent, or Firm*—Andrea G. Reister; Covington & Burling

(57) ABSTRACT

Method of treating warm blooded animals suffering from psychotic disorders. The method includes administering a pharmaceutically effective amount of sustained-release microparticles that include risperidone, or a pharmaceutically acceptable acid addition salt thereof, and a biodegradable and biocompatible polymeric matrix.

20 Claims, 5 Drawing Sheets

U.S. PATENT DOCUMENTS

| | | |
|---|---|---|
| 4,128,641 A | 12/1978 | Itil et al. |
| 4,201,482 A | 5/1980 | Imhauser et al. |
| 4,208,136 A | 6/1980 | King et al. |
| 4,329,331 A | 5/1982 | Kallick et al. |
| 4,335,127 A | 6/1982 | Vandenberk et al. |
| 4,337,261 A | 6/1982 | Shutske et al. |
| 4,342,870 A | 8/1982 | Kennis et al. |
| 4,352,811 A | 10/1982 | Strupczewski |
| 4,389,330 A | 6/1983 | Tice et al. |
| 4,443,451 A | 4/1984 | Kennis et al. |
| 4,458,076 A | 7/1984 | Strupczewski |
| 4,485,107 A | 11/1984 | Kennis et al. |
| 4,489,055 A | 12/1984 | Couvreur et al. |
| 4,511,258 A | 4/1985 | Federighi et al. |
| 4,529,727 A | 7/1985 | Kennis et al. |
| 4,530,840 A | 7/1985 | Tice et al. |
| 4,542,025 A | 9/1985 | Tice et al. |
| 4,585,482 A | 4/1986 | Tice et al. |
| 4,614,440 A | 9/1986 | King et al. |
| 4,616,937 A | 10/1986 | King et al. |
| 4,643,584 A | 2/1987 | Allocca et al. |
| 4,665,075 A | 5/1987 | Vandenberk et al. |
| 4,675,189 A | 6/1987 | Kent et al. |
| 4,677,191 A | 6/1987 | Tankana et al. |
| 4,683,288 A | 7/1987 | Tankana et al. |
| 4,689,330 A | 8/1987 | Janssen et al. |
| 4,696,258 A | 9/1987 | Magrath et al. |
| 4,731,205 A | 3/1988 | McNulty et al. |
| 4,737,500 A | 4/1988 | Sorg et al. |
| 4,753,535 A | 6/1988 | King et al. |
| 4,765,204 A | 8/1988 | Buchholz et al. |
| 4,793,713 A | 12/1988 | King et al. |
| 4,798,786 A | 1/1989 | Tice et al. |
| 4,804,663 A | 2/1989 | Kennis et al. |
| 4,808,007 A | 2/1989 | King et al. |
| 4,835,139 A | 5/1989 | Tice et al. |
| 4,883,666 A | 11/1989 | Sabel et al. |
| 4,897,268 A | 1/1990 | Tice et al. |
| 4,936,689 A | 6/1990 | Federighi et al. |
| 4,940,588 A | 7/1990 | Sparks et al. |
| 4,994,281 A | 2/1991 | Muranishi et al. |
| 5,008,114 A | 4/1991 | Lovrecich |
| 5,075,109 A | 12/1991 | Tice et al. |
| 5,102,872 A | 4/1992 | Singh et al. |
| 5,158,952 A | 10/1992 | Janssen et al. |
| 5,407,609 A | 4/1995 | Tice et al. |
| 5,453,425 A | 9/1995 | Francois et al. |
| 5,478,564 A | 12/1995 | Wantier et al. |
| 5,650,173 A | 7/1997 | Ramstack et al. |
| 5,770,231 A * | 6/1998 | Mesens et al. ............... 424/497 |
| 5,792,477 A | 8/1998 | Rickey et al. |

FOREIGN PATENT DOCUMENTS

| | | |
|---|---|---|
| EP | 0 195 450 | 9/1986 |
| EP | 0 196 132 | 10/1986 |
| EP | 0 248 531 | 12/1987 |
| EP | 0 266 119 | 5/1988 |
| EP | 0368 388 | 5/1990 |
| EP | 0 486 959 | 5/1992 |
| GB | 1 212 730 | 11/1970 |
| GB | 1 351 811 | 3/1974 |
| GB | 2 015 360 | 9/1979 |
| GB | 2 120 113 | 11/1983 |
| GB | 2 246 573 | 2/1992 |
| WO | WO 88/01165 | 2/1988 |
| WO | WO 90/13361 | 11/1990 |
| WO | 91/13595 | 9/1991 |
| WO | WO 91/17772 | 11/1991 |
| WO | WO 94/10982 | 7/1994 |
| WO | WO 94/25460 | 11/1994 |
| WO | WO 95/13799 | 5/1995 |

OTHER PUBLICATIONS

Chang, R. et al., "Dissolution Characteristics of Polycaprolactone–Polylactide Microspheres of Chlorpromazine," *Drug Development and Industrial Pharmacy*, vol. 12, No. 14, 2355–2380 (1986).

Chemineer, "Kenics Static Mixers," *Bulletin* 800: 1–11 (1986).

Chouinard, G. et al., "A Canadian Multicenter Placebo–Controlled Study of Fixed Doses of Risperidone and Haloperidol in the Treatment of Chronic Schizophrenic Patients," *Journal of Clinical Psychopharmacology*, vol. 13, No. 1, 25–40 (1993).

Glazer, W.M. et al., "Depot Neuroleptic Therapy: An Underutilized Treatment Option," *J. Clin. Psychiatry* 53 (12):426–433 (Dec., 1992).

Heinrich, K. et al., "Experimental Comparison of the Efficacy and Compatibility of Risperidone and Clozapine in Acute Schizophrenia," in: Kane, J.M. (ed), Risperidone: Major Progress in Antipsychotic Treatment. *Oxford Clinical Communications*, Oxford: 37–39 (1991).

Janssen and Niemegeers, "Chemistry and pharmacology of compounds related to 4–(4–hydroxy–4–phenyl–piperidino)–butyrophenone," *Arzneim.–Forsch.* (*Drug Res.*) 12:765–767 (1959).

Janssen, P.A.J. et al., "Is it Possible to Predict the Clinical Effects of Neuroleptic Drugs (Major Tranquilizers) from Animal Data!," *Arzneimit. Forsch.* (*Drug Res.*) 10:1196–1206 (1965).

Janssen, P.A.J. et al., "Pharmacology of Risperidone (R 64 766), a New Antipsychotic With Serotonin—$S_2$ and Dopamine—$D_2$ Antagonistic Properties," *The Journal of Pharmacology and Experimental Therapeutics*, vol. 244, No. 2, 685–693 (1988).

Koch Engineering Company Inc., "All Mixing Problems Are Not Alike," 1 page, *Product Brochure*.

Koch Engineering Cmpany Inc., "Static Mixing Technology," Article: 1–15 (1991).

Leysen, J.E., et al., "Biochemical Profile of Risperidone, a New Antipsychotic," *The Journal of Pharmacology and Experimental Therapeutics*, vol. 247, No. 2, 661–670 (1988).

Leyson, J.E. et al., "In vitro receptor binding and neurotransmitter uptake inhibition profile of R 64 766, R 76 477, R 78 543 and 78 544," Janssen Research Foundation, Beerse, Belgium, M 79120, *Preclinical Research Report R 64 766/ 28*, 11 pages (Jan. 1991).

Maulding, H.V. et al., "Biodegradable Microcapsules: Acceleration of Polymeric Excipient Hydrolytic Rate By Incorporation of a Basic Medicament," *Journal of Controlled Release*, 3: 103–117 (1986).

Megen, A.A.H.P. et al., "Comparative Pharmacology of Risperidone, Its Major Metabolite R 76 $477^{(+,)}$ and the Corresponding Enantiomers R 78 543 $^{(+)}$ and R 78 544 $^{(-)}$ in Rats and Dogs," Janssen Research Foundation, Beerse, Belgium, N74694, *Preclinical Research Report* R 64 766/23 (Jun. 1990).

Megens, A.A.H.P. et al., "In Vivo Pharmacological Profile of 9–Hydroxyrisperone, the Major Metabolite of the Novel Anti and Haloperidol," Janssen Research Foundation, Beerse, Belgium, N 96295, *Preclinical Research Report* R 64 766/R 76 477 (May 1993).

Mertens, C., "Long–term treatment of chronic schizophrenic patients with risperidone," in: Kane, J.M. (ed), Risperidone: Major Progress in Antipsychotic Treatment, *Oxford Clinical Communications, Oxford*: 44–48 (1991).

Mutsakis et al., Advances In Static Mixing Technology, *Chemical Engineering Progress*: 42–48 (Jul. 1986).

Niemegeers and Janssen, "A Systemic Study of the Pharmacological Activities of Dopamine Antagonists, " in: *Life Science 24* (24):2201–2216, Pergamon Press Ltd. (1979).

Niemegeers et al., Ántiemetic Specificity of Dopamine Antagonists, *Psychopharmacology* 78:210–213 (1982).

Photocopy of an unofficial English Translation of Japanese Patent Application No. Hei–04 (1992)–332441, "Sustained–Release Microsphere and Process for Producing the Same," filed by Yoshitomi Pharmaceutical Industries, Ltd., which is the priority document of PCT Application No. 94/10982, pp. 1–12.

Ramtoola, Z., et al., "Release Kinetics of Fluphenazine from Biodegradable Microspheres," *Journal of Microencapsulation*, vol. 8, No. 4, 415–423 (1992).

Streiff, F., "In–Line Dispersion and Mass Transfer using Static Mixing Equipment," *Sulzer Technical Review* 3:108–114 (1977).

Suzuki, K. et al., "Microencapsulation and Dissolution Properties of a Neuroleptic in a Biodegradable Polymer, Poly(d, l–lactide)," *Journal of Pharmaceutical Sciences*, vol. 74, No. 1, 21–24 (Jan. 1985).

* cited by examiner

MICROENCAPSULATED 3-PIPERIDINYL-SUBSTITUTED 1,2-BENZISOXAZOLES AND 1,2-BENZISOTHIAZOLES

This application is a continuation of application Ser. No. 09/252,486, filed Feb. 18, 1999 now U.S. Pat. No. 6,110,921, which is a continuation of application Ser. No. 09/005,549, filed Jan. 12, 1998 (now U.S. Pat. No. 5,965,168, which is a continuation of application Ser. No. 08/808,261, filed Feb. 28, 1997 (now U.S. Pat. No. 5,770,231), which is a continuation of application Ser. No. 08/154,403, filed Nov. 19, 1993 now ASN.

BACKGROUND OF THE INVENTION

1. Field of the Invention

The present invention relates to microencapsulated 1,2-benzazoles and their use in the treatment of warm blooded animals suffering from mental illness More particularly, the present invention relates to microencapsulated 3-piperidinyl-substituted 1,2-benzisoxazoles and 1,2-benzisothiazoles and their use in the treatment of mental patients.

2. Description of the Related Art

Strupczewski et al., in U.S. Pat. Nos. 4,352,811 and 4,458,076, describe 3-piperidinyl-1,2-benzisoxazoles and 3-piperidinyl-1,2-benzisothiazoles having antipsychotic and analgesic properties.

Kennis et al., U.S. Pat. No. 4,804,663, disclose 3-piperidinyl-1,2-benzisothiazoles and 3-piperidinyl-1,2-benzisoxazoles and their pharmaceutically acceptable acid addition salts that have antipsychotic properties and are useful in the treatment of a variety of complaints in which serotonin release is of predominant importance. In particular, 3-[2-[4-(6-fluoro-1,2-benzisoxazol-3-yl)-1-piperidinyl)ethyl]-6,7,8,9-tetrahydro-2-methyl-4H -pyrido[1,2-a]pyrimidin -4-one ("Risperidone") is disclosed.

Janssen et al., U.S. Pat. No. 5,158,952, 3-piperidinyl-1.2-benzisoxazoles having long-acting antipsychotic properties and which are useful in the treatment of warm-blooded animals suffering from psychotic diseases. In particular, 3-[2-[4-(6-fluoro-1,2-benzisoxazol-3-yl)-1-piperidinyl)ethyl]-6,7,8,9-tetrahydro-9-hydroxy-2-methyl-4H -pyrido[1,2-a]pyrimidin-4-one ("9-hydroxy-Risperidone") is disclosed.

A number of methods are known by which compounds can be encapsulated in the form of microparticles. In many of these processes, the material to be encapsulated is dispersed in a solvent containing a wall forming material. At a single stage of the process, solvent is removed from the microparticles and thereafter the microparticles product is obtained.

An example of a conventional microencapsulation process and microparticles produced thereby is disclosed in U.S. Pat. No. 3,737,337, incorporated by reference herein, wherein a solution of a wall or shell forming polymeric material in a solvent is prepared. The solvent is only partially miscible in water. A solid or core material is dissolved or dispersed in the polymer-containing solution and, thereafter, the core-material-containing solution is dispersed in an aqueous liquid that is immiscible in the organic solvent in order to remove solvent from the microparticles.

Another example of a process in which solvent is removed from microparticles containing a substance is disclosed in U.S. Pat. No. 3,523,906. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090 organic solvent is evaporated from a dispersion of microparticles in an aqueous medium, preferably under reduced pressure.

Similarly. the disclosure of U.S. Pat. No. 3,891,570 shows a method in which solvent from a dispersion of microparticles in a polyhydric alcohol medium is evaporated from the microparticles by the application of heat or by subjecting the microparticles to reduced pressure.

Another enable of a solvent removal process is shown in U.S. Pat. No. 3,960,757.

Tice et al., in U.S. Pat. No. 4,389,330, describe the preparation of microparticles containing an active agent—which may, inter alia, be a psychotherapeutic agent—by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Tice et al, in U.S. Pat. No. 4,530,840, describe the preparation of microparticles containing an anti-inflammatory active agent by a method comprising: (a) dissolving or dispersing an anti-inflammatory agent in a solvent and dissolving a biocompatible and biodegradable wall forming material in that solvent; (b) dispersing the solvent containing the anti-inflammatory agent and wall forming material in a continuous-phase processing medium; (c) evaporating a portion of the solvent from the dispersion of step (b), thereby forming microparticles containing the anti-inflammatory agent in the suspension: and (d) extracting the remainder of the solvent from the microparticles.

SUMMARY OF THE INVENTION

The present invention relates to microencapsulated 1,2-benzazoles and their use in the treatment of warm blooded animals suffering from mental disease. In a preferred embodiment, the invention relates to a pharmaceutical composition designed for the controlled release of an effective amount of a drug over an extended period of time, prepared in microparticle form. This composition comprises at least one antipsychotic agent and at least one biocompatible, biodegradable encapsulating polymer.

More particularly, the present invention relates to a method of treating warm blooded animals suffering from psychotic disorders comprising the administration thereto of a pharmaceutically effective amount of a biodegradable and biocompatible microparticle composition comprising a 1,2-benzazole of the formula

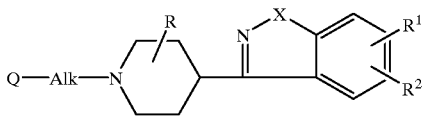

(I)

and the pharmaceutically acceptable acid addition salts thereof, wherein

R is hydrogen or alkyl of 1 to 6 carbon atoms;

$R^1$ and $R^2$ are independently selected from the group consisting of hydrogen, halo, hydroxy, alkyloxy of 1 to 6 carbon atoms, and C alkyl of 1 to 6 carbon atoms;

X is O or S;

Alk is $C_{1-4}$ alkanediyl; and

Q is a radical of formula

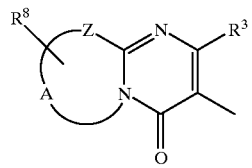

(a)

wherein $R^3$ is hydrogen or alkyl of 1 to 6 carbon atoms:

Z is —S—, —CH$_2$—, or —CR$^4$=CR$^5$—: where $R^4$ and $R^5$ are independently selected from the group consisting of hydrogen or alkyl of 1 to 6 carbon atoms;

A is a bivalent radical —CH$_2$—, CH$_2$—, —CH$_2$—CH$_2$—CH$_2$— or CR$^6$=R$^7$—; where $R^6$ and $R^7$ are independently selected from the group consisting of hydrogen, halo, amino or alkyl of 1 to 6 carbon atoms; and $R^8$ is hydrogen or hydroxyl;

within a polymeric matrix.

In another aspect, the present invention relates to a pharmaceutical composition comprising a biodegradable and biocompatible microparticle composition comprising a 1,2-benzazole of Formula I within a polymeric matrix.

In still another aspect, the present invention relates to a method of inhibiting serotonergic or dopaminergic over-stimulation in animals wherein said method comprises administration of a biodegradable and biocompatible microparticle composition comprising a 1,2-benzazole of Formula I within a polymeric matrix.

DESCRIPTION OF THE PREFERRED EMBODIMENTS

Figure 1:
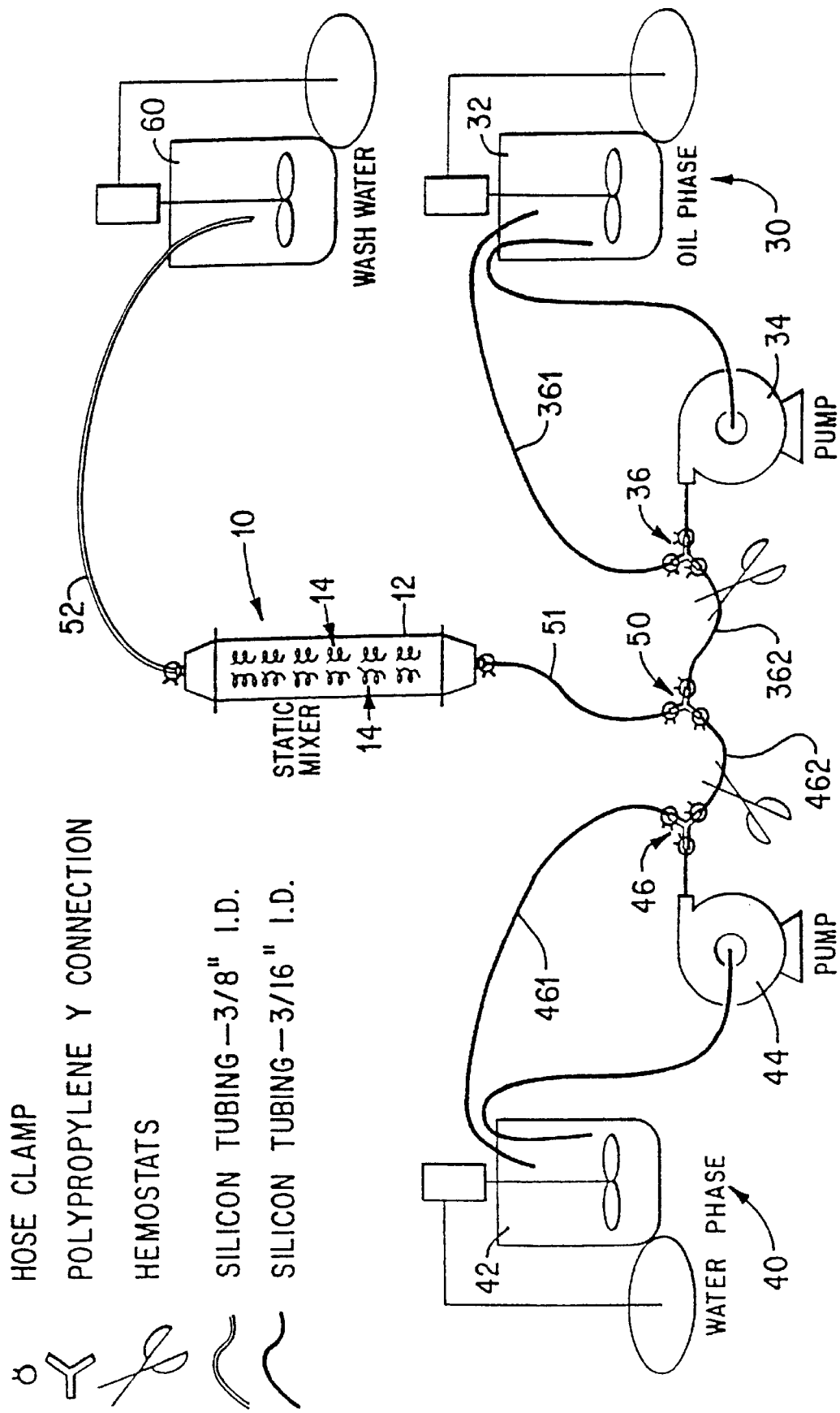
FIG. 1 shows a laboratory set-up for carrying out a preferred process for preparing the microparticles of the present invention.

The present invention is concerned with microencapsulated 1,2-benzazoles having the formula

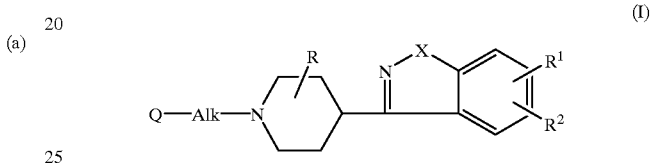

(I)

and the pharmaceutically acceptable acid addition salts thereof, wherein

R is hydrogen or alkyl of 1 to 6 carbon atoms;

$R^1$ and $R^2$ are independently selected from the group consisting of hydrogen, halo, hydroxy, alkyloxy of 1 to 6 carbon atoms and alkyl of 1 to 6 carbon atoms;

X is O or S;

Alk is alkanediyl of 1 to 4 carbon atoms: and

Q is a radical of formula

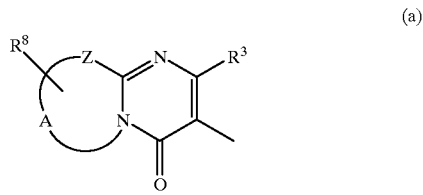

(a)

wherein $R^3$ is hydrogen or alkyl of 1 to 6 carbon atoms;

Z is —S—, —CH$_2$—, or —CR$^4$=CR$^5$—; where $R^4$ and $R^5$ are independently selected from the group consisting of hydrogen or alkyl of 1 to 6 carbon atoms;

A is a bivalent radical —CH$_2$—CH$_2$—, —CH$_2$—CH$_2$—CH$_2$— or CR$^6$=CR$^7$—; where $R^6$ and $R^7$ are independently selected from the group consisting of hydrogen, halo, amino, or alkyl of 1 to 6 carbon atoms; and $R^8$ is hydrogen or hydroxyl.

In the foregoing definitions, the term "halo" is generic to fluoro, chloro, bromo, and iodo; "alkyl of 1 to 6 carbon atoms" is meant to include straight and branched chain saturated hydrocarbon radicals having from 1 to 6 carbon atoms, such as, for example, methyl, ethyl, propyl, butyl, pentyl, hexyl, and isomers thereof; "alkanediyl of 1 to 4 carbon atoms" is meant to include bivalent straight or branched chain alkanediyl radicals having from 1 to 4 carbon atoms, such as, for example, methylene, ethylene, propylene, butylene, and isomers thereof.

Preferred compounds within the invention are those wherein Q is a radical of formula (a) wherein $R^3$ is alkyl of 1 to 6 carbon atoms and A is a bivalent radical —$CH_2$—$CH_2$—, —$CH_2$—$CH_2$—$CH_2$—, or —$CR^6$=$CR^7$—, wherein $R^6$ and $R^7$ are independently selected from the group consisting of hydrogen and alkyl of 1 to 6 carbon atoms.

Particularly preferred compounds are those wherein Q is a radical of formula (a) wherein $R^3$ is alkyl of 1 to 6 carbon atoms and A is a bivalent radical —$CH_2$—$CH_2$—, —$CH_2$—$CH_2$—$CH_2$—, or —$CR^6$=$CR^7$—, wherein $R^6$ and $R^7$ are independently selected from the group consisting of hydrogen and alkyl of 1 to 6 carbon atoms, R is hydrogen, $R^1$ is hydrogen or halo, and $R^2$ is hydrogen, halo, hydroxy, or alkyloxy of 1 to 6 carbon atoms.

More particularly preferred compounds are those wherein R is hydrogen, $R^1$ is hydrogen or halo, and $R^2$ is hydrogen, halo, hydroxy, or alkyloxy of 1 to 6 carbon atoms and Q is a radical of formula (a) wherein —Z—A— is —$CH_2$—$CH_2$—$CH_2$—, —S—$CH_2$—$CH_2$—, —S—$(CH_2)_3$—, —S—$CR^6$=$CR^7$—, or —CH=CH—$CR^6$=$CR^7$—, wherein $R^6$ and $R^7$ are independently selected from the group consisting of hydrogen or methyl;

Especially preferred compounds are those compounds wherein R is hydrogen, $R^1$ is hydrogen, and $R^2$ is hydrogen, halo, hydroxy, or methoxy and Q is a radical of formula (a) wherein —Z—A— is —$CH_2$—$CH_2$—$CH_2$—$CH_2$—, —S—$CH_2$—$CH_2$—, —S—$(CH_2)_3$—, —S—$CR^6$=$CR^7$—, or —CH=CH—$CR^6$=$CR^7$—, wherein $R^6$ and $R^7$ are independently selected from the group consisting of hydrogen or methyl.

The most preferred compounds are selected from the group consisting of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one ("Risperidone") and the pharmaceutically acceptable acid addition salts thereof.

The compounds of formula (I) can generally be prepared by the methods described in U.S. Pat. No. 4,804,663, incorporated herein by reference. These methods comprise reacting an appropriate reactive ester of formula (II) with an appropriately substituted piperidine of formula (III). In the reactive ester (II), W represents a reactive ester moiety such as, for example, halo, e.g., chloro, bromo, or iodo, or a sulfonyloxy group, e.g. methylsulfonyloxy, (4-methylphenyl)sulfonyloxy, and the like.

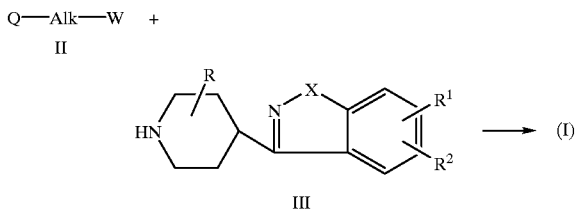

The reaction of (II) with (III) can conveniently be conducted in an inert organic solvent such as, for example, an aromatic hydrocarbon, e.g., benzene, toluene, xylene, and the like; a lower alkanol, e.g., methanol, ethanol, propanol, butanol and isomers thereof; a ketone, e.g., acetone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali or an alkaline earth metal carbonate, bicarbonate, hydroxide, alkoxide, or hydride, e.g., sodium carbonate, sodium bicarbonate, potassium carbonate, sodium hydroxide, sodium methoxide, sodium hydride, and the like, or an organic base such as, for example, a tertiary amine, e.g., N,N-diethylethanamine, N-(1-methylethyl)-2-propanamine, 4-ethylmorpholine, and the like can be used to neutralize the acid liberated during the course of the reaction. In some circumstances, the addition of an iodide salt, preferably an alkali metal iodide, is appropriate. Moderately elevated temperatures can be used to enhance the rate of the reaction.

The compounds of formula (I) can also be prepared following art-known procedures for preparing compounds containing radicals of formula Q within their structure.

The compounds of formula (I) wherein Q is a radical of formula (a), said compounds being represented by the formula (I-a), can be prepared following art-known cyclizing procedures for preparing pyrimidin-4-ones, such as, for example, by reacting an amine of formula (VI) with a cyclizing agent of formula (VII) or by cyclizing a reagent of formula (VII) with an amine of formula (IX).

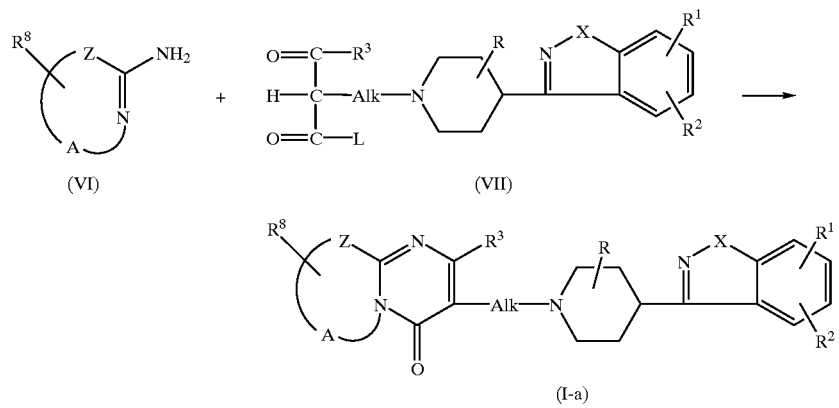

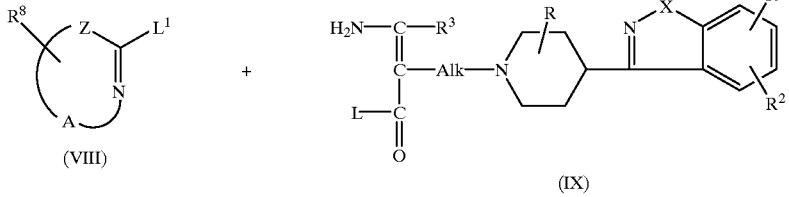

(VIII)      (IX)

In the foregoing reaction schemes, L and L¹ each independently represent an appropriate leaving group such as, for example, ($C_{1-6}$ alkyl)oxy, hydroxy, halo, amino, mono- and di($C_{1-6}$ alkyl)amino, and the like.

Following the same cyclization procedure the compounds of formula (I-a) can also be prepared by cyclizing an intermediate of formula (IX) with a reagent of formula (X).

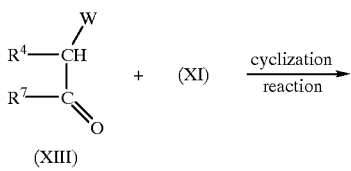

The compounds of formula (I-a) wherein Z is S, said compounds being represented by the formula (I-a-1), can also be prepared by cyclizing a 2-mercaptopyrimidinone of formula (XI) with a reagent of formula (XII).

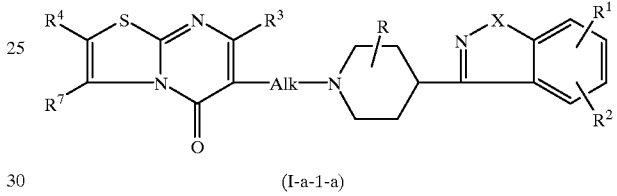

(XIII)

(I-a-1-a)

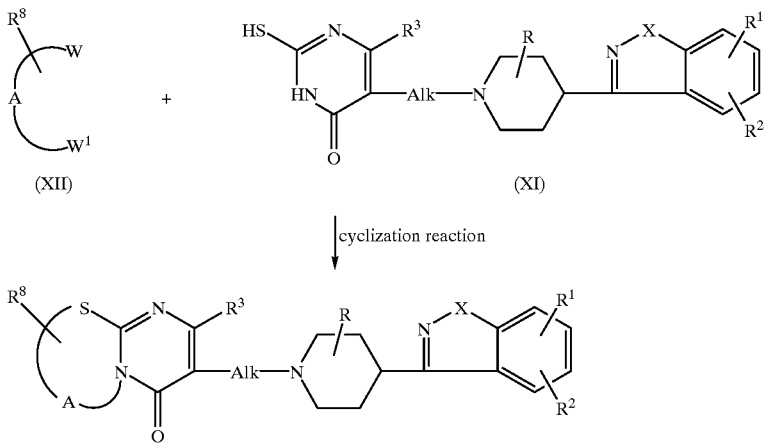

(XII)      (XI)

↓ cyclization reaction

In (XII), $W^1$ has the same meaning as previously described for W.

The compounds of formula (I-a-1) wherein A is

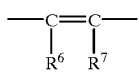

said compounds being represented by the formula (I-a-1-a), can also be prepared by cycling a 2-mercaptopyrimidinone of formula (XI) with a reagent of formula (XIII).

The cyclization reactions described above can be carried out as described above.

The compounds of formula (I) have basic properties and, consequently, can be converted to their therapeutically active non-toxic acid addition salt forms by treatment with appropriate acids, such as, for example, inorganic acids, such as hydrohalic acid, e.g., hydrochloric, hydrobromic, and the like; sulfuric acid, nitric acid, phosphoric acid, and the like; or organic acids, such as, for example, acetic, propanoic, hydroacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, toluenesulfonic, cyclohexanesulfamic, 2-hydroxybenzoic, 4-amino-2-hydroxybenzoic, and the like acids. Conversely the salt form can be converted by treatment with alkali into the free base form.

A number of intermediates and starting materials in the foregoing preparations are known compounds that can be prepared according to art-known methodologies. For example, the intermediates of formula (II) and their preparations are described in U.S. Pat. Nos. 4,335,127; 4,342,870; 4,443,451; and 4,485,107.

The intermediates of formula (III) can generally be derived from a benzoylpiperidine of formula

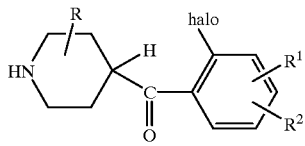

(XIV)

wherein halo is preferably fluoro, following art-known procedures, e.g., by reacting the benzoylpiperidine (XIV) with hydroxylamine and cyclizing the thus obtained oxime

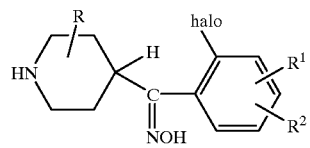

(XV)

following art known procedures, thus obtaining the intermediate of formula (III) wherein X is O, said intermediates being represented by the formula

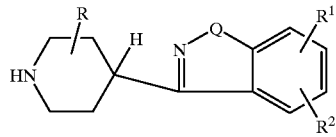

(III-a)

The intermediates of formula (III) wherein X is S, said intermediates being represented by the formula

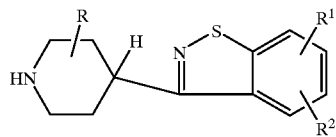

(III-b)

can be prepared following a procedure analogous to that described in U.S. Pat. No. 4,458,076.

The compounds of formula (I) and the pharmaceutically acceptable acid addition salts thereof are potent antagonists of a series of neurotransmitters and, as a result, have useful pharmacological properties. In particular, the compounds of formula (I) and their pharmaceutically acceptable acid addition salts possess strong psychotic activity and antiserotonin activity.

Janssen et al. (*The Journal of Pharmacology and Experimental Therapeutics* 244 (2):685–693 (1988)) made comparative studies of risperidone with ritanserin, a selective centrally acting serotonin-$S_2$ antagonist and with haloperidol, a selective centrally acting dopamine-$D_2$ antagonist. They reported that risperidone, like ritanserin, showed activity in all tests related to serotonin-$S_2$ antagonism, but at even lower doses. Like haloperidol, risperidone also showed activity in all tests related to dopamine-$D_2$ antagonism. They concluded that, qualitatively, risperidone is a mixed serotonin-dopamine antagonist.

Owing to their pharmacological activities, the compounds of formula (I) and their pharmaceutically acceptable acid addition salts are used in the treatment of psychotic diseases and in the treatment of a variety of complaints in which serotonin release is of predominant importance such as, for example, in the blocking of serotonin-induced contractions of bronchial tissues and of blood vessels, arteries as well as veins. The subject compounds are also useful as sedating, anxiolytic, anti-aggressive, anti-stress, muscular protectant and cardiovascular protectant agents and, consequently, are useful for protecting warm-blooded animals, for example, in stress situations. Additionally, these compounds are useful for protection against endotoxine shocks and as antidiarrheals.

In view of the usefulness of the subject compounds in the treatment of psychotic diseases, it is evident that the present invention provides a method of treating warm-blooded animals suffering from psychotic disorders, said method comprising the systemic administration of a pharmaceutically effective amount of a microencapsulated compound of formula (I) or a pharmaceutically acceptable acid addition salt thereof in admixture with a pharmaceutical carrier. In general, it is contemplated that an effective amount of the compound, per se, would be from 0.01 mg/kg to 4 mg/kg body weight, more preferably, from 0.04 mg/kg to 2 mg/kg body weight.

In order to provide a clear and consistent understanding of the specification and claims, including the scope to be given such terms, the following definitions are provided.

By the term "administered" is intended any method of delivering the 1,2-benzazole-containing microparticles of the invention to a warm blooded animal, such as, for example, parenteral (intravenous, intramuscular, or subcutaneous) administration.

By "microparticles" is meant solid particles that contain an active agent, herein the 1,2-benzazole, either in solution or in crystalline form. The active agent is dispersed or dissolved within the polymer that serves as the matrix of the particle.

The present invention concerns a method of treating mental illness in warm blooded animals, preferably mammals, more preferably humans, (hereinafter, collectively referred to as "patients") that comprises providing to such patients biodegradable microparticles loaded with a 1,2-benzazole, as described above. The method of the present invention provides advantages over methods known in the art, such as, inter alia, a biodegradable system, an injectable system that prevents the loss of dose during treatment, the ability to mix microparticles containing different drugs, and the ability to program release (multiphasic release patterns) to give faster or slower rates of drug release as needed.

The product of the present invention offers the advantage of durations of action ranging from 7 to more than 200 days, depending upon the type of microparticle selected. In a preferred embodiment, the microparticles are designed to afford treatment to patients over a period of 30 to 60 days.

The duration of action can be controlled by manipulation of the polymer composition, polymer:drug ratio, and microparticle size.

Another important advantage of the present invention is that practically all of the active agent is delivered to the patient because the polymer used in the method of the invention is biodegradable, thereby permitting all of the entrapped agent to be released into the patient.

A method for preparing the microparticles of the invention is also described in both U.S. Pat. Nos. 4,389,330 and 4,530,840, fully incorporated herein by reference.

The polymeric matrix material of the microparticles of the present invention is a biocompatible and biodegradable polymeric material. The term "biocompatible" is defined as a polymeric material that is not toxic to the human body, is not carcinogenic, and does not significantly induce inflammation in body tissues. The matrix material should be biodegradable in the sense that the polymeric material should degrade by bodily processes to products readily disposable by the body and should not accumulate in the body. The products of the biodegradation should also be biocompatible with the body in the same sense that the polymeric matrix is biocompatible with the body. Suitable examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

In a preferred embodiment, administration of the 1,2-benzazoles to patients by the method of the invention is achieved by a single administration of the drug loaded microparticles, releasing the drug in a constant or pulsed manner into the patient and eliminating the need for repetitive injections.

The formulation of the present invention contains an antipsychotic agent dispersed in a microparticle matrix material. The amount of agent incorporated in the microparticles usually ranges from about 1 wt % to about 90 wt. %, preferably 30 to 50 wt. %, more preferably 35 to 40 wt. %. By weight % is meant parts of agent per total weight of microparticle. For example, 10 wt. % agent would mean 10 parts agent and 90 parts polymer by weight.

The molecular weight of the polymeric matrix material is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric material being used, it is very difficult to specify an appropriate molecular weight range for all polymers. The molecular weight of a polymer is also important from the point of view of its influence upon the biodegradation rate of the polymer. For a diffusional mechanism of drug release, the polymer should remain intact until all of the drug is released form the microparticles and then degrade. The drug can also be released from the microparticles as the polymeric excipient bioerodes. By an appropriate selection of polymeric materials a microparticle formulation can be made in which the resulting microparticles exhibit both diffusional release and biodegradation release properties. This is useful in affording multiphasic release patterns.

The microparticle product of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the agent and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. A preferred solvent for use in the practice of the present invention is a mixture of benzyl alcohol and ethyl acetate.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic phase must be largely immiscible. The continuous-phase processing medium most commonly employed is water, although nonaqueous media, such as, xylene, toluene, and synthetic and natural oils can be used. Usually, a surfactant is added to the continuous-phase processing medium to prevent the microparticles from agglomerating and to control the size of the solvent microdroplets in the emulsion. A preferred surfactant-dispersing medium combination is a 0.1 to 10 wt. %, more preferably 0.5 to 2 wt. % solution of poly(vinyl alcohol) in water. The dispersion is formed by mechanical agitation of the mixed materials. An emulsion can also be formed by adding small drops of the active agent-wall forming material solution to the continuous phase processing medium. The temperature during the formation of the emulsion is not especially critical, but can influence the size and quality of the microparticles and the solubility of the agent in the continuous phase. Of course, it is desirable to have as little of the agent in the continuous phase as possible. Moreover, depending on the solvent and continuous-phase processing medium employed, the temperature must not be too low or the solvent and processing medium will solidify or become too viscous for practical purposes. On the other hand, it must not be so high that the processing medium will evaporate or that the liquid processing medium will not be maintained. Moreover, the temperature of the medium cannot be so high that the stability of the particular active agent being incorporated in the microparticles is adversely affected. Accordingly, the dispersion process can be conducted at any temperature that maintains stable operating conditions, preferably about 20° C. to about 60° C., depending upon the agent and excipient selected.

The dispersion formed is stable and from this dispersion the organic phase fluid can be partially removed in the first step of the solvent removal process. The solvent can easily be removed by common techniques, such as heating, the application of a reduced pressure, or a combination of both. The temperature employed to evaporate solvent from the microdroplets is not critical, but should not be so high as to degrade the agent employed in the preparation of a given microparticle or to evaporate solvent at a rate rapid enough to cause defects in the wall forming material. Generally, from 10 to 90%, preferably 40 to 60% of the solvent is removed in the first solvent removal step.

After the first stage, the dispersed microparticles in the solvent immiscible fluid medium are isolated from the fluid medium by any convenient means of separation. Thus, for example, the fluid can be decanted from the microparticles or the microparticle suspension can be filtered. Various other combinations of separation techniques can be used, if desired.

Following the isolation of the microparticles from the continuous-phase processing medium, the remainder of the solvent in the microparticles is removed by extraction. In this step, the microparticles can be suspended in the same continuous-phase processing medium used in step one, with or without surfactant, or in another liquid. The extraction medium removes the solvent from the microparticles, but does not dissolve them. During the extraction, the extraction medium containing dissolved solvent must be removed and replaced with fresh extraction medium. This is best done on a continual or continuous basis where the rate of extraction medium replenishment is critical. If the rate is too slow, agent crystals may protrude from the microparticles or grow in the extraction medium. Obviously, the rate of extraction medium replenishment for a given process is a variable that can easily be determined at the time the process is performed and, therefore, no precise limits for the rate may be predetermined. After the remainder of the solvent has been removed, the microparticles are dried by exposure to air or by other conventional drying techniques, such as, vacuum drying, drying over a desiccant, or the like. This process is very efficient in encapsulating the agent since core loadings of up to 80 wt. %, preferably up to 50 wt. % cam be obtained.

A more preferred method of encapsulating the active agent to form the controlled release microparticles of the present invention involves the use of static mixers, in the method disclosed by our co-worker, Paul F. Herbert, in co-pending U.S. patent application Ser. No. 08/154,409, filed of even date herewith.

Static or motionless mixers consist of a conduit or tube in which is received a number of static mixing elements. Static mixers provide homogeneous mixing in a relatively short length of conduit, and in a relatively short period of time. With static mixers, the fluid moves through the mixer, rather than some part of the mixer, such as a blade, moving through the fluid. A static mixer is more fully described in U.S. Pat. No. 4,511,258, which is incorporated herein by reference.

When using a static mixer to form an emulsion, a variety of factors determine emulsion particle size. These factors include the density and viscosity of the various solutions or phases to be mixed, volume ratio of the phases, interfacial tension between the phases, static mixer parameters (conduit diameter; length of mixing element; number of rating elements), and linear velocity through the static mixer. Temperature is a variable because it affects density, viscosity, and interfacial tension. The controlling variables are linear velocity, shear rate, and pressure drop per unit length of static mixer. Particularly, droplet size decreases as linear velocity increases and droplet size increases as pressure drop decreases. Droplets will reach an equilibrium size after a fixed number of elements for a given flow rate. The higher the flow rate, the fewer elements needed. Because of these relationships scaling from laboratory batch sizes to commercial batch sizes is reliable and accurate, and the same equipment can be used for laboratory and commercial batch sizes.

In order to create microparticles containing an active agent, an organic phase and an aqueous phase are combined. The organic and aqueous phases are largely or substantially immiscible, with the aqueous phase constituting the continuous phase of the emulsion. The organic phase includes an active agent as well as a wall forming polymer or polymeric matrix material. The organic phase can be prepared by dissolving an active agent in an organic or other suitable solvent, or by forming a dispersion or an emulsion containing the active agent. In the more preferred process used in the practice of the present invention, the organic phase and the aqueous phase are pumped so that the two phases are simultaneously flowing through a static mixer, thereby forming an emulsion, which comprises microparticles containing the active agent encapsulated in the polymeric matrix material. The organic and aqueous phases are pumped through the static mixer into a large volume of quench liquid. The quench liquid may be plain water, a water solution, or other suitable liquid. Organic solvent may be removed from the microparticles while they are being washed or being stirred in the quench liquid. After the microparticles are washed in a quench to extract or remove the organic solvent, they are isolated, as through a sieve, and dried.

A laboratory set up for carrying out a static mixer process is illustrated in FIG. 1. An organic or oil phase 30 is prepared by dissolving and, optionally, heating an active agent and a polymeric matrix material or polymer in a stirred pot 32 on a hot plate. However, the process of the present invention is not limited to preparing organic phase 30 by dissolving an active agent. Alternatively, organic phase 30 may be prepared by dispersing an active agent in a solution containing a polymeric matrix material. In such a dispersion, the active agent is only slightly soluble in organic phase 30. Alternative, organic phase 30 may be prepared by preparing an emulsion containing an active agent and a polymeric matrix material (double emulsion process). In the double emulsion process, a primary emulsion is prepared which contains an active agent and a polymeric matrix material (organic phase 30). The primary emulsion may be a water-in-oil emulsion, an oil-in-water emulsion, or any suitable emulsion. The primary emulsion (organic phase 30) and an aqueous phase are then pumped through a static mixer to form a second emulsion which comprises microparticles containing the active agent encapsulated in the polymeric matrix material.

Organic phase 30 is pumped out of stirred pot 32 by a magnetically driven gear pump 34. The discharge of pump 34 feeds a "Y" connection 36. One branch 361 of "Y" connection 36 returns to pot 32 for recirculation flow. The other branch 362 feeds into an in-line static mixer 10. Aqueous or water phase 40 is prepared in like manner, with a stirred pot 42, a magnetically driven gear pump 44, and a "Y" connection 46. One branch 461 of "Y" connection 46 returns to pot 42 for recirculation flow. The other branch 462 feeds into in-line static mixer 10. Organic phase 30 and aqueous phase 40 are substantially immiscible.

Branches 362 and 462 from each solution which feed in-line static mixer 10 are joined by another "Y" connection 50 and feed through mixer inlet line 51 into static mixer 10. Static mixer 10 discharges through mixer outlet line 52 into wash tank 60. Silicone tubing and polypropylene fittings are used in the system illustrated in FIG. 1. Silicone tubing having ⅜ inch ID is used for all lines except mixer outlet line 52. Smaller diameter tubing (3/16 inch ID) is used for mixer outlet line 52 to prevent collapse of the emulsion both in mixer outlet line 52 and upon entering wash tank 60.

In one embodiment of the process, pumps 34 and 44 are started in recirculation mode and desired flow rates are set for organic phase 30 and water phase 40. The flow rate of water phase 41) is preferably greater than the flow rate of organic phase 30. However, the two flow rates may be substantially the same. The ratio of the flow rate of water phase 40 to the flow rate of organic phase 30 is preferably in the range of 1:1 to 10:1. "Y" connection 46 is then switched so that water phase 40 flows through branch 462 to static mixer 10. Once water phase 40 fills mixer inlet line 51, static mixer 10, and mixer outlet line 52, "Y" connection 36 is switched so that organic phase 30 flows through branch 362 to static mixer 10. Organic phase 30 and aqueous phase 40 are now flowing simultaneously through static mixer 10. When the desired volume of organic phase has been pumped to static mixer 10, "Y" connection 36 is switched to recirculation through branch 361. Water phase 40 continues to flow for a short time to clean out any organic phase remaining in mixer inlet line 51, static mixer 10, and mixer outlet line 52. "Y" connection 46 is then switched to recirculation through branch 461.

Organic phase 30 and aqueous phase 40 are mixed in static mixer 10 to form an emulsion. The emulsion formed comprises microparticles containing the active agent encapsulated in the polymeric matrix material. The microparticles produced by the method of the present invention are usually of a spherical shape, although they may be irregularly shaped. The microparticles produced by the method of the present invention can vary in size, ranging from submicron to millimeter diameters. In a preferred embodiment of the present invention, static mixing elements 14 of static mixer 10 are selected so that the resulting microparticles range in size from 1 to 500 microns ($\mu$m), more preferably 25 to 180 microns. whereby administration of the microparticles can be carried out with a standard gauge needle. The microparticles may be stirred in wash tank 60 which contains a quench liquid. The microparticles may be isolated from the quench liquid, such as by using a sieve column. The microparticles may be dried using conventional drying techniques, and further size isolation may be done.

The active agent bearing microparticles are obtained and stored as a dry material. Prior to administration to a patent, the dry microparticles can be suspended in an acceptable pharmaceutical liquid vehicle, preferably a 2.5 wt. % solution of carboxymethyl cellulose, whereupon the suspension is injected into the desired portion of the body.

The microparticles can be mixed by size or by type so as to provide for the delivery of active agent to the patient in a multiphasic manner and/or in a manner that provides different agents to the patient at different times, or a mixture of agents at the same time.

The following examples further describe the materials and methods used in carrying out the invention. The examples are not intended to limit the invention in any manner.

EXAMPLE 1

A mixture of 5.3 parts of 3-(2-chloromethyl)-6,7,8,9-tetrahydro-2-methyl-4H-pyrido[1,2-a]pyrimidin-4-one monohydrochloride, 4.4 parts of 6-fluoro-3-(4-piperidinyl)-1,2-benzisoxazole, 8 parts of sodium carbonate, 0.1 part of potassium iodide, and 90 parts of DMF is stirred overnight at 80°–90° C. After cooling, the reaction mixture is poured into water. The product is filtered off and crystallized from a mixture of DMF and 2-propanol. The product is filtered off and dried, yielding 3.8 parts (46%) of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one; mp. 170.0° C.

EXAMPLE 2

Preparation of 35% Theoretically Loaded Risperidone Microparticles (Batch Prodex 2)

First, the aqueous phase (solution A) is prepared by weighing and mixing 906.1 g 1% poly(vinyl alcohol). (Vinyl 205, Air Products and Chemical Inc., Allentown, Pa.), 29.7 g benzyl alcohol (J. T. Baker, Phillipsburg, N.J.) end 65.3 g ethyl acetate (Fisher Scientific, Fair Lawn, N.J.). Then the organic phase (solution B) is prepared by dissolving 29.3 g of high viscosity 75:25 dl (polylactide-co-glycolide), (commercially available from Medisorb Technologies International, L.P., Cincinnati, Ohio) in 108.7 g ethyl acetate and 108.4 g benzyl alcohol. Once the polymer is completely dissolved, 15.7 g risperidone base (Janssen Pharmaceutica, Beerse, Belgium) is added and dissolved in the polymer solution. The exposure time of the dissolved risperidone with the polymer is kept to a minimum (<10 minutes). Solutions A and B are then pumped through a ¼ inch diameter static mixer (Cole Parmer L04667-14) via a gear drive pump and head (Cole Parmer L07149-04, L07002-16) at flow rates of 198 and 24 ml/minute, respectively, into a quench composed of 55 liters of water for injection containing 1276.0 g of ethyl acetate, 92.3 g (0.02 Molar) of anhydrous sodium bicarbonate, and 116.2 g (0.02 Molar) of anhydrous sodium carbonate (Mallinckrodt Specialty Chemicals, Paris, Ky.) at 11° C. The microparticles are allowed to stir in the first wash for 1.75 hours, then isolated by sieving with a 25-micron sieve. The product retained by the sieve is transferred to a 20-liter wash at 13° C. After stirring in the sieved wash for 2.25 hours, the microparticles are isolated and size fractionated by sieving through a stainless steel sieve column composed of 25- and 180-micron mesh sizes. The microparticles are dried overnight, then collected and weighed.

EXAMPLE 3

Preparation of 40% Theoretically Loaded Risperidone Microparticles (Batch Prodex 3)

First, the aqueous phase (solution A) is prepared by weighing and mixing 904.4 g 1% poly (vinyl alcohol). (Vinyl 205. Air Products and Chemical Inc. Allentown. Pa.), 30.1 g benzyl alcohol (J. T. Baker, Phillipsburg, N.J.) and 65.8 g ethyl acetate (Fisher Scientific, Fair Lawn, N.J.). Then the organic phase (solution B) is prepared by dissolving 27.1 g of high viscosity 75:25 dl (polylactide-co-glycolide), (Medisorb Technologies International, L. P., Cincinnati, Ohio) in 99.3 g ethyl acetate and 99.1 g benzyl alcohol. Once the polymer is completely dissolved, 18.1 g risperidone base (Janssen Pharmaceutica, Beerse, Belgium) is added and dissolved in the polymer solution. The exposure time of the dissolved risperidone with the polymer is kept to a minimum (<10 minutes). Solutions A and B are then pumped through a ¼ inch diameter static mixer (Cole Parmer L04667-14) via a gear drive pump and head (Cole Parmer L07149-04, L07002-16) at flow rates of 198 and 24 ml/minute, respectively, and into a quench composed of 55 liters of water for injection containing 1375.6 g of ethyl acetate, 92.4 g (0.02 Molar) of anhydrous sodium bicarbonate, and 116.6 g (0.02 Molar) of anhydrous sodium carbonate (Mallinckrodt Specialty Chemicals, Paris, Ky.) at 12° C. The microparticles are allowed to stir in the first wash for 2 hours, then isolated by sieving with a 25-micron sieve. The product retained by the sieve is transferred to a 20-liter wash at 12° C. After stirring in the sieved wash for 3 hours, the microparticles are isolated and size fractionated by sieving through a stainless-steel sieve column composed of 25- and 180-micron mesh sizes. The microparticles are dried overnight, then collected and weighed.

EXAMPLE 4

Lyophilization and Gamma Irradiation of Microparticles from Batches Prodex 2 and Prodex 3 (Samples Prodex 4A, Prodex 4B, and Prodex 4C)

Microparticles from batches Prodex 2 and Prodex 3 were lyophilized. The microparticles were weighed into 5 cc serum vials. Then an aqueous vehicle composed of 0.75% CMC, 5% Mannito, and 0.1% Tween 80 was added to the vials. The microparticles were suspended in the vehicle by agitation, then quickly frozen in a dry ice/acetone bath. The vials were then lyophilized in a pilot-scale lyophilizer (Dura Stop Microprocessor Control, FTS Systems, Inc., Stone Ridge, N.Y.) employing a ramped 30° C. maximum temperature cycle for 50 hours. Samples Prodex 4A and Prodex 4C were lyophilized samples from Prodex 2 and Prodex 3, respectively. Sample Prodex 4B was lyophilized from Prodex 2 that had been subsequently sterilized by 2.2 MRad gamma irradiation from a $^{60}$Co source.

In Vitro Dissolution Studies

In vitro dissolution studies were conducted on Prodex 2, Prodex 3, Prodex 4A, Prodex 4B, and Prodex 4C. Real time and accelerated methodologies were used. The equipment consisted of a Hanson research 6-cell USP paddle (Method II) dissolution apparatus interfaced with a spectrophotometer and data station. Receiving media were continuously recirculated from each cell to flow cells inside the spectrophotometer (absorbance maximum of 236 nm).

Figure 2:
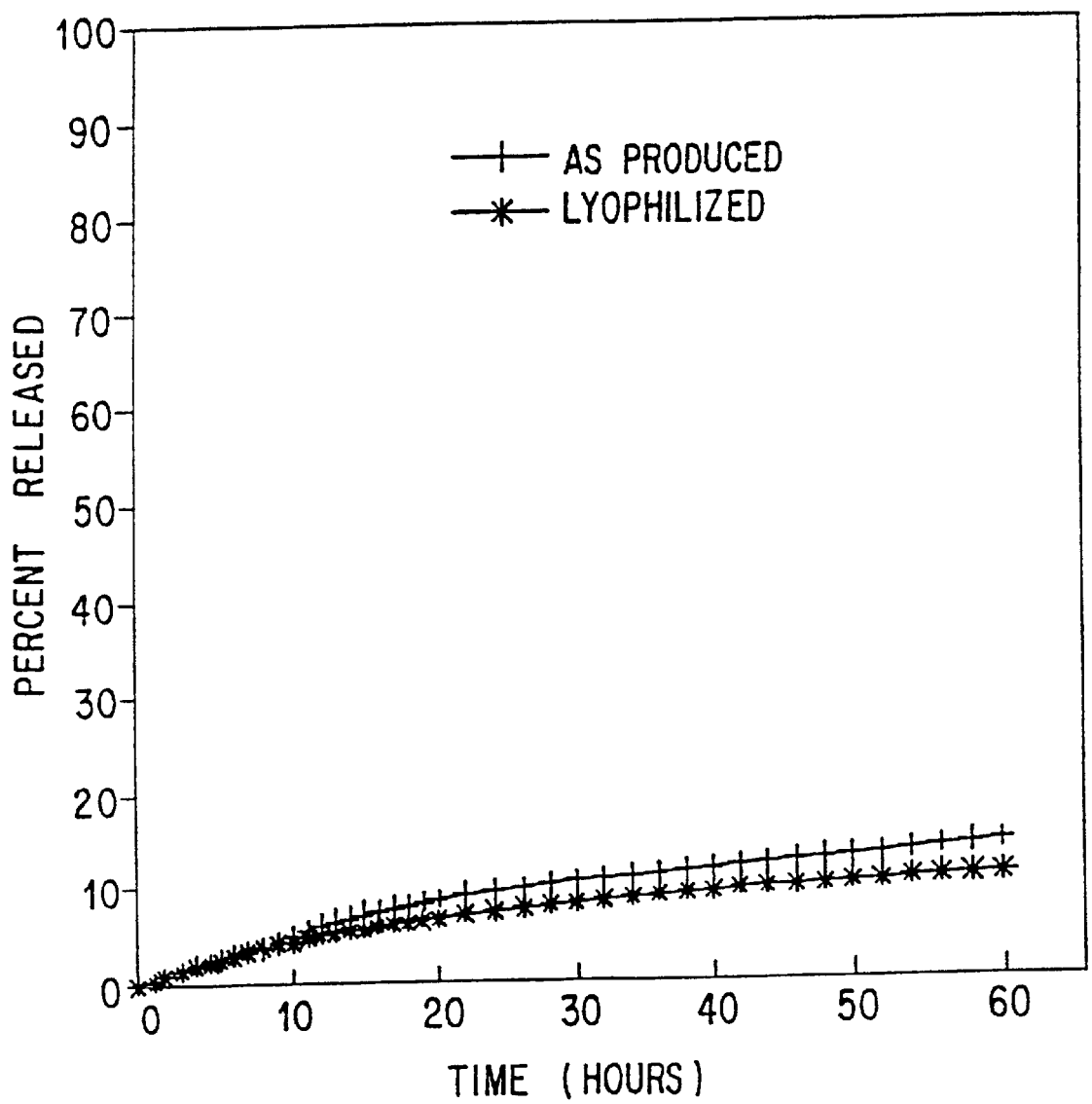
FIG. 2 depicts a graph of in vitro dissolution data for risperidone microparticles of batch Prodex 3, both as produced and lyophilized.
Figure 3:
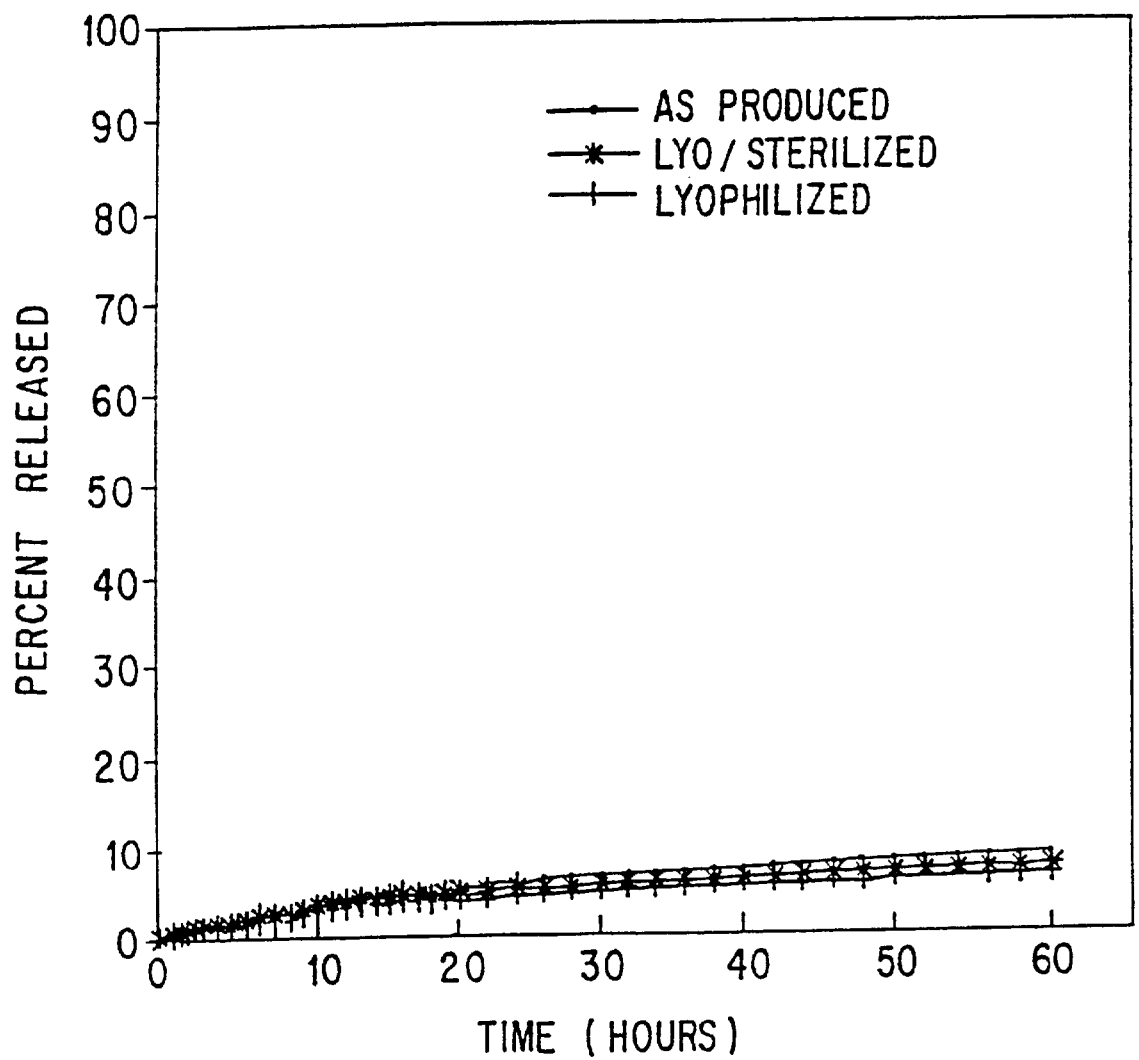
FIG. 3 depicts a graph of in vitro dissolution data for risperidone microparticles of batch Prodex 2, both as produced and lyophilized.

The real time model measured the release rates of microparticles into a receiving medium consisting of 50 mM tris buffer at pH 7.4 at 37° C. Risperidone was found to have sufficient solubility ($\geq 0.5$ mg/ml) to allow in vitro experiments with this receiving medium. The amount of risperidone was kept below 20% of saturation to provide infinite sink conditions. Data are shown in FIGS. 2 and 3.

Figure 4:
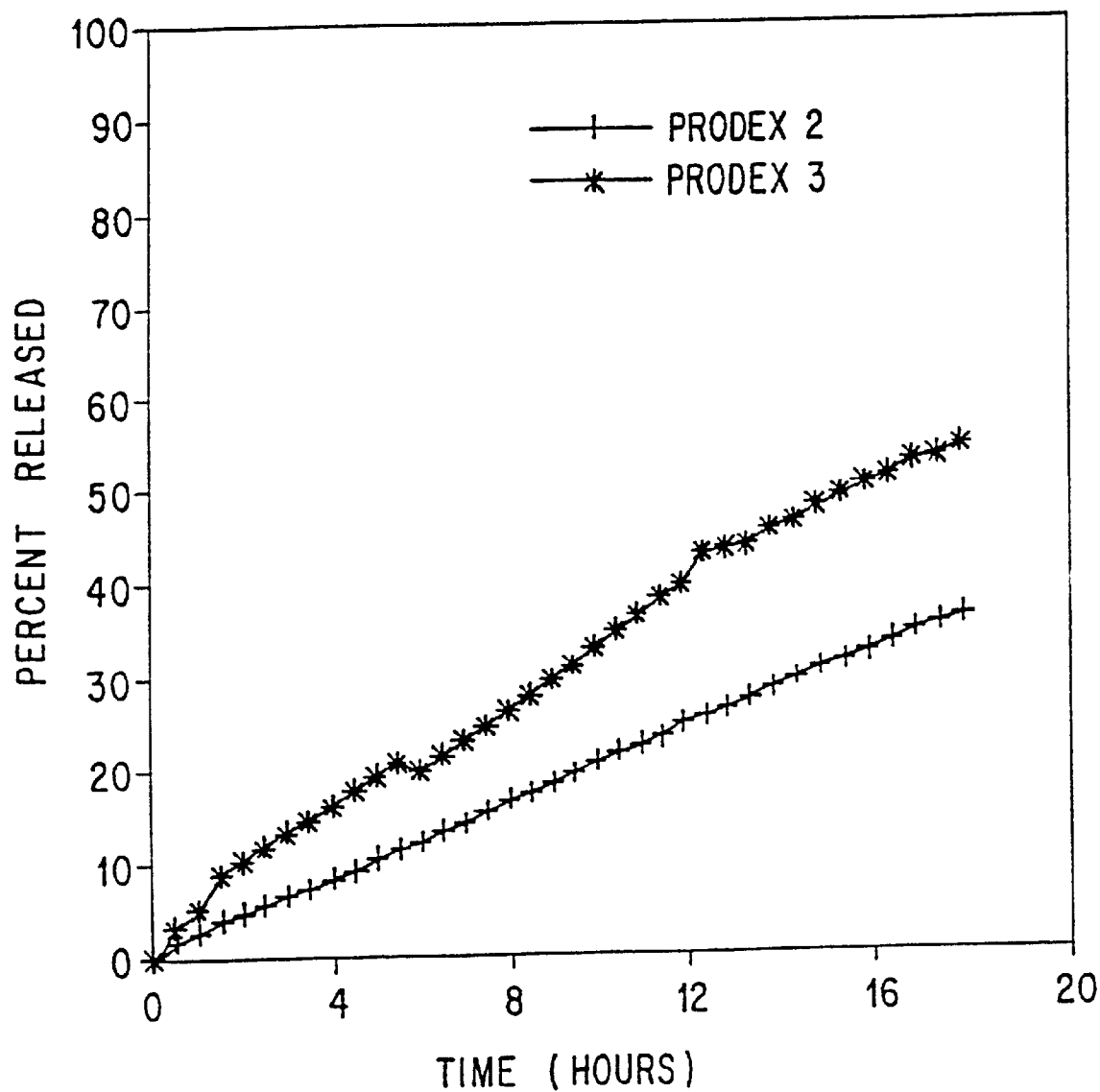
FIG. 4 depicts a graph of accelerated in vitro dissolution data for risperidone microparticles of batches Prodex 3 and Prodex 2.

An accelerated model was also developed. A receiving medium of 27.5 wt % ethanol was used. Results are shown in FIG. 4.

Animal Dosing and Blood Sampling

In vivo studies in dogs were conducted on product provided as dry microparticles (Prodex 2, Prodex 3) and in lyophilized form (Prodex 4A, Prodex 4B, Prodex 4C). The dry microparticles were syringe-loaded and resuspended in the syringe with an injection vehicle comprised of 2.5 wt % carboxymethyl cellulose (CMC). The lyophilized samples (Prodex 4A, Prodex 4B, Prodex 4C) were reconstituted in WFI (water for injection) prior to injection.

Male and female dogs, weighing 11.6±2.3 kg, were divided into groups of three dogs each. The dogs were housed in groups of three and fed according to standard laboratory conditions.

The appropriate volumes of the respective depot formulations were dosed intramuscularly into the biceps femoralis of the left hind limb at the level of the thigh of the dogs at a dose of approximately 2.5 mg/kg risperidone.

Blood samples (5 ml on EDTA) were taken from one of the jugular veins at 0 (predose), 1, 5, and 24 hours after dosing and also on days 4, 7, 11, 14, 18, 23, 25, 28, 32, 35, 39, 42, 46, 49, 53, and 56 at the time of the apomorphine vomiting test. The apomorphine test was described by P. A. J. Janssen and C. J. E. Niemegeers in *Arzneim.-Forsch.* (*Drug Res.*), 9.765–767 (1959). If, during the course of the experiments. each of the three dogs of a group no longer showed protection against apomorphine-induced vomiting, blood sampling was discontinued. Blood samples were centrifuged at 3000 rpm for 10 min and plasma was separated. The plasma samples were stored at $\leq 20°$ C. until analysis.

Plasma samples were analyzed for risperidone (RISP) and for 9-hydroxyrisperidone (9-OH RISP) using radioimmunoassay (RIA). For the plasma samples analyzed with RIA, two different RIA procedures were used, one for unchanged risperidone and the other for the active moiety (sum of risperidone and 9-hydroxy-risperidone, not to be confused with the term "active agent" used elsewhere herein). For the latter plasma samples, the concentrations of 9-hydroxy-risperidone were calculated as the difference between the concentrations of the active moiety and those of risperidone. The quantification limits for the RIA methods were 0.20 ng/ml for risperidone and 0.50 ng/ml for the active moiety.

For each of the formulations, mean (±S.D., n=3) plasma concentrations of risperidone, 9-hydroxy-risperidone, and of the active moiety, were calculated. Ratios of the plasma concentrations of 9-hydroxy-risperidone to those of risperidone were calculated where possible. Peak plasma concentrations and peak times of risperidone, 9-hydroxy-risperidone, and their sum were determined by visual inspection of the data. AUC ("area under the curve") values of risperidone and 9-hydroxy-risperidone were calculated between zero time and time using the trapezoidal rule. The time t is the last time point at which concentrations of risperidone or 9-hydroxy-risperidone were higher than the limit of quantification in at least 1 out of 3 dogs. For dogs belonging to the same formulation group, AUCs were calculated up to the same end-time t, using the value of the quantification limit, if one concentration was lower than the quantification limit. If two consecutive concentrations were lower than the quantification limit, the concentration of the earlier sampling point was set equal to the quantification limit, and the concentration of the later sampling point was taken as zero. The AUCs were not extrapolated to infinity. The AUC of the active moiety was calculated as the sum of the AUCs of risperidone and 9-hydroxy-risperidone.

Figure 5:
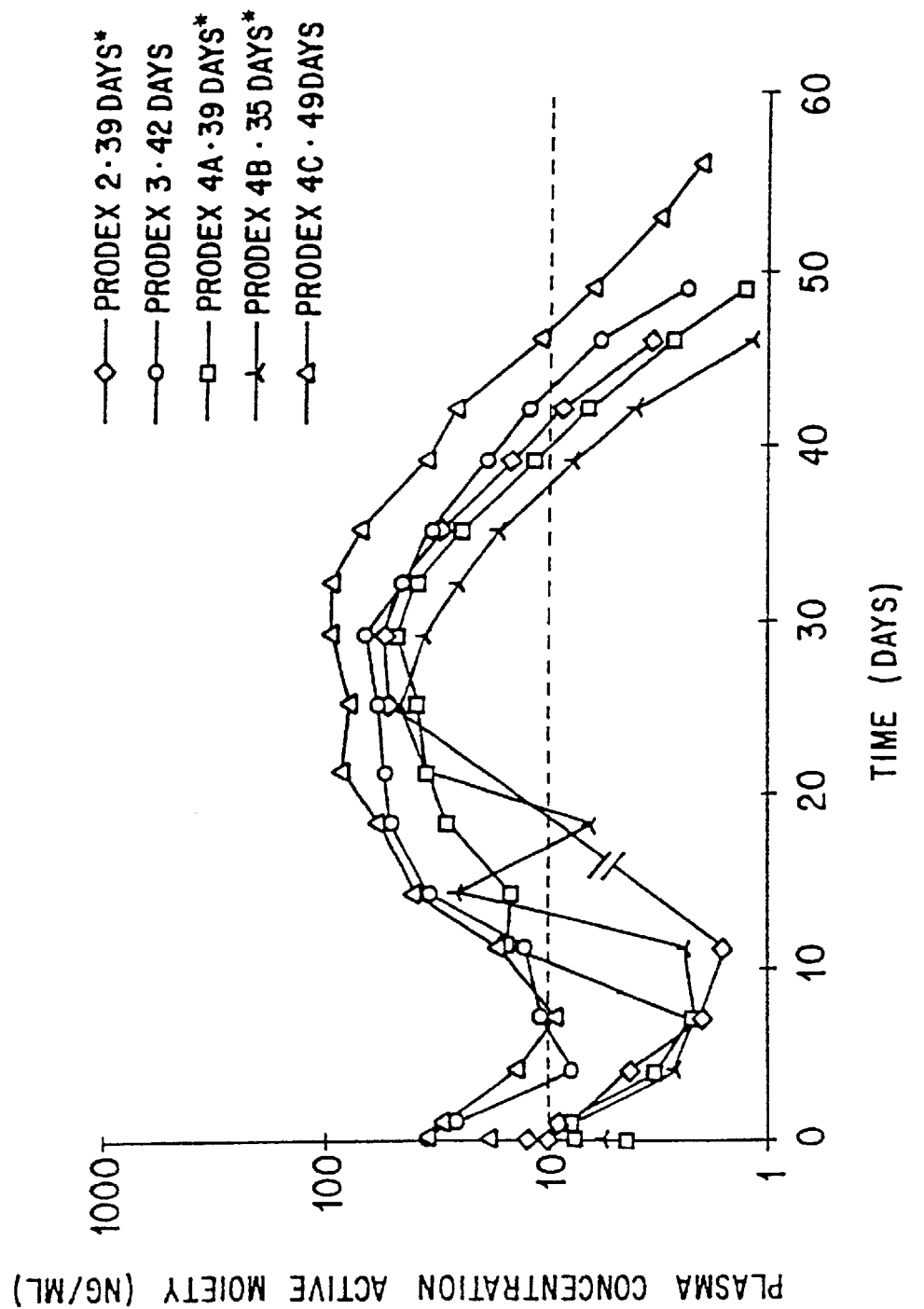
FIG. 5 depicts a graph of mean (n=2) plasma concentration-time curves for the active moiety (sum of risperidone and 9-hydroxy risperidone) after single intramuscular administration to beagle dogs of risperidone depot formulations at an approximate dose of 2.5 mg/kg. The period of anti-emetic activity (in at least 2 out of 3 dogs) in the apomorphine vomiting test is given in the legend for each of the formulations. An asterisk (*) indicates that the anti-emetic activity is interrupted in at least 2 out of 3 dogs at the beginning of the study. The broken line indicates an approximate lowest minimum plasma concentration necessary for anti-emetic activity. The // sign indicates that for formulation Prodex 2 no blood was sampled on days 14, 18, and 21.

Mean or median plasma concentrations and/or pharmacokinetic parameters of risperidone, 9-hydroxy-risperidone, and the active moiety for formulations Prodex 2/3/4A/4B/4C, are given in Table 1. Mean plasma concentration-time curves for formulations Prodex 2/3/4A/4B/4C are in FIG. 5. For each of the formulation groups, results are first discussed for risperidone, then for 9-hydroxy-risperidone, and at last for the active moiety. For the active moiety, plasma concentrations are related to the anti-emetic effect in the apomorphine vomiting test.

After administration of formulations Prodex 2 up to Prodex 4C, mean peak plasma levels of risperidone were low. They were attained at largely different time points. The further release of risperidone from the different formulations proceeded gradually and was long-lasting. This resulted in low plasma concentrations of both risperidone and its metabolite. Mean peak times for 9-hydroxy-risperidone all ranged from 26 to 30 days. The plasma concentration-time profile of the active moiety was similar for formulations Prodex 2 up to Prodex 4C. At the beginning of the experiment, plasma concentrations of the active moiety showed a peak within 1 or 2 days, due to a rapid initial release of risperidone. The peak was followed by a decrease of the concentrations with a dip at 5–8 days. From day 8 on, concentrations increased again until day 20, after which time they remained at a more or less constant level during a period of, on average, 15 days. During this period, for each of the formulations, concentrations of the active moiety showed a second peak and concentrations were higher than for the first peak. The anti-emetic activity lasted 35 to 42 days for formulations Prodex 2, Prodex 4A, and Prodex 4B. For formulation Prodex 4C, it lasted 49 days, but without interruption in any of the dogs. The longest activity of formulation Prodex 4C paralleled the highest $C_{max}$, $T_{max}$, and $AUC_{0-t}$ for the active moiety, in comparison with the other 4 formulations of the same group.

The duration of action of these microparticle-based risperidone formulations in the apomorphine-induced emesis test in dogs was also studied. Neuroleptics antagonized apomorphine-induced emesis by blocking dopamine $D_2$ receptors in the area postrema of the fourth ventricle. The test is generally used to predict the onset and duration of antipsychotic action of neuroleptics in man (Janssen et al. *Arzneim.-Forsch./Drug Res.* 15: 1196–1206 (1965); Niemegeers et al., *Life Sci.* 24:2201–2216 (1979)). 9-OH-risperidone has a pharmacological profile that is virtually identical to that of its parent compound. Parent compound and active metabolite constitute together the "active moiety" that determines the biological activity of risperidone.

Apomorphine was administered subcutaneously at 0.31 mg/kg to the dogs twice a week, during the whole course of the experiment. The dogs were observed for vomiting during a 1-hour period after the administration of apomorphine. Complete absence of emesis for 1 hour after apomorphine challenge was considered to reflect significant anti-emetic activity. The duration of the anti-emetic action was defined as the time interval during which 2 out of 3 dogs were protected from emesis.

The formulations were injected in a volume of 0.5 ml into the biceps femoralis of one of the hind limbs at the level of the thigh. At several time intervals after the intramuscular injection, blood samples were taken and, immediately thereafter, the dogs were challenged with a dose of apomorphine. Complete absence of emesis within 1 h after apomorphine challenge (which is never observed in control animals; n>1000) was considered to reflect significant anti-emetic activity.

Table 2 indicates whether the dogs were protected (+) or not protected (−) from apomorphine-induced emesis at the various time intervals after intramuscular injection of the depot formulations. All formulations showed an immediate onset of anti-emetic action.

TABLE 1

Mean (±S.D.; n = 3) or median plasma concentrations and mean (±S.D.; n = 3) pharmacokinetic parameters of risperidone, 9-hydroxy-risperidone, and their sum (= the "active moiety") after intramuscular administration of risperidone depot formulations at 2.5 mg/kg to beagle dogs.

| | Prodex 2 | | Prodex 3 | | Prodex 4A | |
|---|---|---|---|---|---|---|
| Times (days) | RISP | 9-OH RISP | RISP | 9-OH RISP | RISP | 9-OH RISP |
| 0 | <0.20 | ≦0.50 | ≦0.20 | ≦0.50 | ≦0.20 | ≦0.50 |
| 0.042 (1 h) | 8.36 ± 1.06 | 4.17 ± 1.71 | 21.4 ± 8.8 | 14.4 ± 9.1 | 3.25 ± 0.57 | 1.18 ± 0.50 |
| 0.208 (5 h) | 2.87 ± 0.20 | 7.34 ± 2.02 | 7.55 ± 3.38 | 27.4 ± 22.0 | 2.61 ± 0.60 | 5.13 ± 1.08 |
| 1 | 1.25 ± 0.72 | 6.92 ± 3.88 | 2.90 ± 1.70 | 23.0 ± 17.8 | 1.13 ± 0.24 | 7.82 ± 3.55 |
| 4 | 0.67 ± 0.61 | 4.36 ± 3.32 | 1.22 ± 0.77 | 6.58 ± 3.07 | 0.74 ± 0.38 | 2.54 ± 1.20 |
| 7 | 0.35* | 1.65 ± 1.24 | 1.96 ± 1.70 | 8.79 ± 6.72 | 0.39* | 1.90 ± 1.52 |
| 11 | 0.41 ± 0.15 | 1.16 ± 0.35 | 1.52 ± 0.91 | 11.2 ± 11.7 | 2.46 ± 3.55 | 12.7 ± 20.2 |
| 14 | —** | —** | 4.36 ± 1.99 | 29.4 ± 25.0 | 2.23 ± 1.19 | 12.6 ± 15.0 |
| 18 | — | — | 6.33 ± 2.48 | 44.1 ± 35.4 | 4.28 ± 1.41 | 23.3 ± 12.5 |
| 21 | — | — | 8.61 ± 2.25 | 44.8 ± 26.3 | 6.97 ± 1.57 | 27.1 ± 11.3 |
| 25 | 6.79 ± 1.74 | 44.6 ± 13.6 | 9.08 ± 3.95 | 47.9 ± 19.5 | 6.03 ± 1.50 | 32.3 ± 2.8 |
| 29 | 6.84 ± 3.19 | 46.0 ± 15.1 | 9.26 ± 5.27 | 54.2 ± 33.6 | 6.52 ± 1.40 | 40.2 ± 3.6 |
| 32 | 4.97 ± 1.89 | 39.5 ± 36.6 | 5.60 ± 2.78 | 38.8 ± 25.2 | 3.81 ± 1.72 | 35.2 ± 16.3 |
| 35 | 3.61 ± 1.84 | 25.8 ± 11.5 | 4.70 ± 3.39 | 28.4 ± 21.9 | 2.55 ± 1.31 | 22.1 ± 14.4 |
| 39 | 1.44 ± 0.51 | 13.0 ± 7.1 | 2.01 ± 1.47 | 16.4 ± 9.6 | 1.13 ± 0.82 | 10.4 ± 6.4 |
| 42 | 1.05 ± 0.45 | 7.73 ± 3.77 | 1.31 ± 0.79 | 10.7 ± 6.5 | 0.68* | 6.08 ± 4.26 |
| 46 | ≦0.20* | 2.94 ± 1.35 | 0.45* | 5.55 ± 4.04 | ≦0.20* | 2.48 ± 1.81 |
| 49 | — | — | 0.23* | 2.13 ± 1.34 | ≦0.20 | 1.23* |
| 53 | — | — | — | — | — | — |
| 56 | — | — | — | — | — | — |
| $C_{max}$ (ng/ml) | 8.61 ± 1.41 | 61.0 ± 19.7 | 21.4 ± 8.8 | 56.3 ± 32.2 | 7.75 ± 0.78 | 43.9   6.6 |
| $T_{max}$ (days) | 10 ± 17 | 29 ± 4 | 0.042 ± 0.000 | 26 ± 2 | 25 ± 4 | 30 ± 2 |
| $AUC_{0-1}$ (ng · h/ml) | 3212 ± 914 | 21496 ± 4854 | 5048 ± 2397 | 30632 ± 19866 | 3280 ± 576 | 19632 ± 8274 |
| t (days) | 46 | 46 | 49 | 49 | 46 | 49 |
| | RISP + 9-OH RISP | | RISP + 9-OH RISP | | RISP + 9-OH RISP | |
| $C_{max}$ (ng/ml) | 67.3 ± 19.8 | | 66.0 ± 37.0 | | 49.6 ± 6.7 | |
| $T_{max}$ (days) | 29 ± 4 | | 26 ± 2 | | 30 ± 2 | |
| $AUC_{0-1}$ (ng · h/ml) | 24708 ± 5341 | | 35680 ± 22261 | | 22912 ± 8822 | |

| | Prodex 4B | | Prodex 4C | |
|---|---|---|---|---|
| Time (days) | RISP | 9-OH RISP | RISP | 9-OH RISP |
| 0 | ≦0.20 | ≦0.50 | ≦0.20 | ≦0.50 |
| 0.042 (1 h) | 3.32 ± 0.75 | 2.53 ± 0.79 | 15.5 ± 5.2 | 3.32 ± 2.18 |
| 0.208 (5 h) | 1.52 ± 0.33 | 5.56 ± 2.43 | 15.1 ± 7.7 | 19.2 ± 6.2 |
| 1 | 1.22 ± 0.58 | 7.10 ± 3.40 | 4.49 ± 1.04 | 25.0 ± 7.1 |
| 4 | 0.58* | 2.25 ± 1.00 | 2.06 ± 0.42 | 12.1 ± 2.5 |
| 7 | 0.35* | 1.78* | 1.47 ± 0.29 | 7.96 ± 0.74 |

TABLE 1-continued

Mean (±S.D.; n = 3) or median plasma concentrations and mean (±S.D.; n = 3) pharmacokinetic parameters of risperidone, 9-hydroxy-risperidone, and their sum (= the "active moiety") after intramuscular administration of risperidone depot formulations at 2.5 mg/kg to beagle dogs.

| 11 | 0.53* | 1.87* | 3.23 ± 1.72 | 13.4 ± 4.6 |
|---|---|---|---|---|
| 14 | 4.06 ± 3.47 | 22.1 ± 20.3 | 7.67 ± 4.54 | 30.9 ± 17.8 |
| 18 | 1.41 ± 0.14 | 5.13 ± 0.85 | 8.15 ± 4.69 | 48.5 ± 34.5 |
| 21 | 4.22 ± 4.98 | 27.1 ± 21.1 | 13.1 ± 9.4 | 69.3 ± 41.4 |
| 25 | 5.39 ± 3.41 | 41.0 ± 29.7 | 8.37 ± 0.88 | 67.8 ± 28.0 |
| 29 | 4.66 ± 1.47 | 31.1 ± 13.3 | 13.8 ± 5.2 | 77.9 ± 17.7 |
| 32 | 3.50 ± 1.81 | 21.4 ± 9.8 | 10.3 ± 4.5 | 80.9 ± 51.3 |
| 35 | 1.91 ± 0.71 | 14.9 ± 4.5 | 7.58 ± 3.49 | 61.4 ± 15.1 |
| 39 | 0.67 ± 0.16 | 7.15 ± 2.47 | 3.90 ± 1.34 | 31.2 ± 10.7 |
| 42 | ≦0.20* | 3.83 ± 0.40 | 2.97 ± 1.35 | 23.2 ± 13.7 |
| 46 | ≦0.20* | 1.08 ± 0.53 | 0.68 ± 0.39 | 10.4 ± 6.3 |
| 49 | — | — | 0.26* | 6.04 ± 3.75 |
| 53 | — | — | ≦0.20* | 2.98 ± 2.39 |
| 56 | — | — | ≦0.20* | 1.89 ± 1.40 |
| $C_{max}$ (ng/ml) | 7.71 ± 4.23 | 42.6 ± 27.3 | 16.3 ± 6.6 | 95.4 ± 41.7 |
| $T_{max}$ (days) | 24 ± 5 | 26 ± 2 | 0.097 ± 0.096 | 30 ± 2 |
| $AUC_{0-1}$ (ng · h/ml) | 2648 ± 1199 | 15656 ± 8104 | 7424 ± 3018 | 46840 ± 19125 |
| t (days) | 46 | 46 | 56 | 56 |

| | RISP + 9-OH RISP | RISP + 9-OH RISP |
|---|---|---|
| $C_{max}$ (ng/ml) | 48.5 ± 29.8 | 108 ± 44 |
| $T_{max}$ (days) | 26 ± 2 | 30 ± 2 |
| $AUC_{0-1}$ (ng · h/ml) | 18311 ± 9222 | 54264 ± 22055 |

*Median value.
**No blood sampling from day 14 until day 25 of the experiment, due to absence of protection against apomorphine-induced vomiting. Concentrations in italics indicate antiemetic activity in at least 2 out of 3 dogs.

TABLE 2

Protection (+) or no protection (−) from apomorphine-induced emesis in dogs at successive time intervals after intramuscular administration of microparticle-based depot formulations of the antipsychotic risperidone at an approximate dose level of 2.5 mg/kg

| Form. | Prodex 2 | | | Prodex 3 | | | Prodex 4A | | | Prodex 4B | | | Prodex 4C | | |
|---|---|---|---|---|---|---|---|---|---|---|---|---|---|---|---|
| Dog Weight (kg) | 14.2 | 11.5 | 9.8 | 12.9 | 12.4 | 13.4 | 10.0 | 12.3 | 9.2 | 9.7 | 8.6 | 10.6 | 13.2 | 16.4 | 16.2 |
| Volume (ml/dog) | $0.5^3$ | $0.5^3$ | $0.5^3$ | $0.5^3$ | $0.5^3$ | $0.5^3$ | $0.5^3$ | $0.5^3$ | $0.5^3$ | $0.5^3$ | $0.5^3$ | $0.5^3$ | $0.5^3$ | $0.5^3$ | $0.5^3$ |
| Dose (mg/kg) | 2.5 | 2.5 | 2.8 | 2.5 | 2.5 | 2.5 | 2.5 | 2.3 | 2.6 | 2.5 | 2.5 | 2.6 | 2.4 | 2.4 | 2.5 |
| Route | im | im | im | im | im | im | im | im | im | im | im | im | im | im | im |
| 1 h | + | + | − | + | + | + | + | + | + | − | + | + | + | + | + |
| 5 h | + | + | + | + | + | + | + | + | + | + | − | + | + | + | + |
| 1 d | + | + | + | + | + | + | + | + | + | + | + | + | + | + | + |
| 4 d | − | − | + | + | − | + | + | + | − | − | − | + | + | + | + |
| 7 d | − | − | − | − | + | + | − | − | − | − | − | + | + | + | + |
| 11 d | − | − | − | + | + | + | + | + | − | − | − | + | + | + | + |
| 14 d | | | | + | + | + | + | + | + | + | + | + | + | + | + |
| 18 d | | | | + | + | + | + | + | + | + | + | + | + | + | + |
| 21 d | | | | + | + | + | + | + | + | + | + | + | + | + | + |
| 25 d | + | + | + | + | + | + | + | + | + | + | + | + | + | + | + |
| 29 d | + | + | + | + | + | + | + | + | + | + | + | + | + | + | + |
| 32 d | + | + | + | + | + | + | + | + | + | + | + | + | + | + | + |
| 35 d | + | + | + | + | + | + | + | + | + | + | + | + | + | + | + |
| 39 d | − | + | + | + | − | + | + | − | − | − | − | − | + | + | + |
| 42 d | − | − | − | + | + | + | − | − | − | − | − | − | + | + | − |
| 46 d | − | − | − | + | − | − | − | − | − | − | − | − | + | + | − |
| 49 d | | Stop | | − | − | − | − | − | − | | Stop | | + | + | − |
| 53 d | | | | | Stop | | | Stop | | | | | − | + | − |
| 56 d | | | | | | | | | | | | | − | − | − |
| | | | | | | | | | | | | | | Stop | |

[3]Injection volume: 0.5 ml/dog; the concentration of the microparticles was adapted to the body weight.

What is claimed is:

1. A method of treating warm blooded animals suffering from psychotic disorders comprising the administration thereto of a pharmaceutically effective amount of sustained-release microparticles produced by dissolving in a solvent an active agent and a biodegradable and biocompatible polymer to form an organic phase, wherein the active agent is selected from the group consisting of risperidone, 9-hydroxy-risperidone, and pharmaceutically acceptable acid addition salts of the foregoing, and extracting the solvent to form microparticles.

2. A method of treating warm blooded animals suffering from psychotic disorders comprising the administration thereto of a pharmaceutically effective amount of sustained-release microparticles comprising risperidone, or a pharmaceutically acceptable acid addition salt thereof, in crystalline form, and a biodegradable and biocompatible polymeric matrix.

3. The method of claim 1, wherein the microparticles range in size from 1 to 500 microns.

4. The method of claim 2, wherein the microparticles range in size from 1 to 500 microns.

5. The method of claim 1, wherein the microparticles range in size from 25 to 180 microns.

6. The method of claim 2, wherein the microparticles range in size from 25 to 180 microns.

7. The method of claim 1, wherein the microparticles are formulated in a liquid injection vehicle.

8. The method of claim 2, wherein the microparticles are formulated in a liquid injection vehicle.

9. The method of claim 7, wherein the liquid injection vehicle is selected from the group consisting of physiological saline solution and an aqueous solution of carboxymethyl cellulose with a surfactant.

10. The method of claim 8, wherein the liquid injection vehicle is selected from the group consisting of physiological saline solution and an aqueous solution of carboxymethyl cellulose with a surfactant.

11. The method of claim 1, wherein the microparticles are administered by intra-muscular injection.

12. The method of claim 2, wherein the microparticles are administered by intra-muscular injection.

13. The method of claim 1, wherein the microparticles are administered by subcutaneous injection.

14. The method of claim 2, wherein the microparticles are administered by subcutaneous injection.

15. The method of claim 3, wherein the microparticles comprise a plurality of sizes to provide for delivery of the active agent in a multi-phasic manner.

16. The method of claim 4, wherein the microparticles comprise a plurality of sizes to provide for delivery of the active agent in a multi-phasic manner.

17. The method of claim 1, wherein a portion of the microparticles exhibit diffusional release and a portion of the microparticles exhibit biodegradation release.

18. The method of claim 2, wherein a portion of the microparticles exhibit diffusional release and a portion of the microparticles exhibit biodegradation release.

19. The method of claim 17, wherein a portion of the microparticles exhibit both diffusional release and biodegradation release.

20. The method of claim 18, wherein a portion of the microparticles exhibit both diffusional release and biodegradation release.

* * * * *

(12) EX PARTE REEXAMINATION CERTIFICATE (5967th)
United States Patent
Mesens et al.

(10) Number: US 6,368,632 C1
(45) Certificate Issued: *Oct. 23, 2007

(54) MICROENCAPSULATED 3-PIPERIDINYL-SUBSTITUTED 1,2-BENZISOXAZOLES AND 1,2-BENZISOTHIAZOLES

(75) Inventors: Jean Mesens, Wechelderzande (BE); Michael E. Rickey, Loveland, OH (US); Thomas J. Atkins, York, PA (US)

(73) Assignee: Alkermes Controlled Therapeutics, Inc. II, Cambridge, MA (US)

Reexamination Request:
No. 90/008,151, Aug. 28, 2006

Reexamination Certificate for:
Patent No.: 6,368,632
Issued: Apr. 9, 2002
Appl. No.: 09/578,908
Filed: May 26, 2000

(*) Notice: This patent is subject to a terminal disclaimer.

Related U.S. Application Data

(63) Continuation of application No. 09/252,486, filed on Feb. 18, 1999, now Pat. No. 6,110,921, which is a continuation of application No. 09/005,549, filed on Jan. 12, 1998, now Pat. No. 5,965,168, which is a continuation of application No. 08/808,261, filed on Feb. 28, 1997, now Pat. No. 5,770,231, which is a continuation of application No. 08/154,403, filed on Nov. 19, 1993, now abandoned.

(51) Int. Cl.
*A61K 9/16* (2006.01)
*A61K 31/517* (2006.01)
*A61K 31/505* (2006.01)
*A61K 31/519* (2006.01)

(52) U.S. Cl. .................. 424/489; 424/486; 424/497; 424/501; 514/964; 514/965; 514/259.41

(58) Field of Classification Search .............. None
See application file for complete search history.

(56) References Cited

U.S. PATENT DOCUMENTS

| | | |
|---|---|---|
| 3,773,919 A | 11/1973 | Boswell et al. |
| 4,384,975 A | 5/1983 | Fong |
| 4,389,330 A | 6/1983 | Tice et al. |
| 4,530,840 A | 7/1985 | Tice et al. |
| 4,804,663 A | 2/1989 | Kennis et al. |
| 4,940,588 A | 7/1990 | Sparks et al. |
| 5,158,952 A | 10/1992 | Janssen et al. |

FOREIGN PATENT DOCUMENTS

| | | |
|---|---|---|
| GB | 2 265 311 | 9/1993 |
| WO | 91/02527 | 3/1991 |

OTHER PUBLICATIONS

Z. Ramtoola et al., J. Microencapsulation 9(4): pp. 415–423 (1992).*
R. Bodmeier et al, Inter. J. Pharmaceutica 43: pp. 179–186 (1988).*
Suzuki et al., "Microencapsulation and Dissolution Properties of a Neuroleptic in Biodegradable Polymer, Poly(d, l–lactide)," *J. Pharm. Sci.*, Vo. 74, No. 1, pp. 21–24, Jan. 1985 ("Suzuki").
Chang et al., "Dissolution Characteristics of Polycaprolactone–Polylactide Microspheres of Chlorpromazine," *Drug Dev. & Inds. Pharm.*, 12(14), pp. 2355–2380, 1986 ("Chang").

* cited by examiner

*Primary Examiner*—Bennett Celsa

(57) ABSTRACT

Method of treating warm blooded animals suffering from psychotic disorders. The method includes administering a pharmaceutically effective amount of sustained-release microparticles that include risperidone, or a pharmaceutically acceptable acid addition salt thereof, and a biodegradable and biocompatible polymeric matrix.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 2 are determined to be patentable as amended.

Claims 3–20, dependent on an amended claim, are determined to be patentable.

1. A method of treating warm blooded animals suffering from psychotic disorders comprising the administration thereto *by injection* of a pharmaceutically effective amount of sustained-release microparticles produced by dissolving in a solvent an active agent and a biodegradable and biocompatible polymer to form an organic phase, wherein the active agent is selected from the group consisting of risperidone, 9-hydroxy-risperidone, and pharmaceutically acceptable acid addition salts of the foregoing, and extracting the solvent to form microparticles, *wherein the sustained-release microparticles provide release of the active agent over a period of at least seven days.*

2. A method of treating warm blooded animals suffering from psychotic disorders comprising the administration thereto *by injection* of a pharmaceutically effective amount of sustained-release microparticles comprising risperidone, or a pharmaceutically acceptable acid addition salt thereof, in crystalline form, and a biodegradable and biocompatible polymeric matrix, *wherein the sustained microparticles provide release of the risperidone, or the pharmaceutically acceptable acid addition salt thereof, over a period of at least seven days.*

\* \* \* \* \*